US009080947B2

(12) United States Patent
Yamazui et al.

(10) Patent No.: US 9,080,947 B2
(45) Date of Patent: Jul. 14, 2015

(54) X-RAY IRRADIATION DEVICE AND ANALYSIS DEVICE

(75) Inventors: Hiromichi Yamazui, Kanagawa (JP); Keisuke Kobayashi, Ibaraki (JP); Hideo Iwai, Ibaraki (JP); Masaaki Kobata, Ibaraki (JP)

(73) Assignees: National Institute for Materials Science, Ibaraki (JP); Ulvac-PHI, Inc., Kanagawa (JP)

( * ) Notice: Subject to any disclaimer, the term of this patent is extended or adjusted under 35 U.S.C. 154(b) by 297 days.

(21) Appl. No.: 13/638,197

(22) PCT Filed: Mar. 30, 2011

(86) PCT No.: PCT/JP2011/001904
§ 371 (c)(1),
(2), (4) Date: Oct. 2, 2012

(87) PCT Pub. No.: WO2011/122020
PCT Pub. Date: Oct. 6, 2011

(65) Prior Publication Data
US 2013/0016813 A1 Jan. 17, 2013

(30) Foreign Application Priority Data
Mar. 31, 2010 (JP) .................... 2010-080669

(51) Int. Cl.
*G21K 1/06* (2006.01)
*G01N 23/227* (2006.01)
(Continued)

(52) U.S. Cl.
CPC .............. *G01N 23/2273* (2013.01); *G21K 1/06* (2013.01); *G21K 7/00* (2013.01); *H01J 35/28* (2013.01);
(Continued)

(58) Field of Classification Search
CPC ....................................... G01N 23/2273
USPC ............................................ 378/82–85
See application file for complete search history.

(56) References Cited

U.S. PATENT DOCUMENTS 3,772,522 A * 11/1973 Hammond et al. ............ 378/84
5,164,975 A * 11/1992 Steinmeyer .................... 378/85
(Continued)

FOREIGN PATENT DOCUMENTS

JP           4-53548 U      5/1992
JP           7-325052 A     12/1995
(Continued)

OTHER PUBLICATIONS

Kobata, M. et al. "Development of the Hard-X-ray Angle Resolved X-ray Photoemission Spectrometer for Laboratory Use" *Analytical Sciences*, Feb. 2010, 26:227-232.
(Continued)

*Primary Examiner* — Michael Maskell
(74) *Attorney, Agent, or Firm* — Saliwanchik, Lloyd & Eisenschenk

(57) ABSTRACT

[Object] The present invention provides an X-ray irradiation device capable of adjusting the energy of X-rays in a wide range, and an analysis device equipped with the X-ray irradiation device.
[Solving Means] An X-ray irradiation device according to an embodiment of the present invention focuses X-rays emitted from an X-ray generation mechanism to a predetermined focal position by a focusing mechanism. The X-ray generation mechanism has a structure which generates a plurality of X-rays having different wavelengths. The focusing mechanism has a structure in which the plurality of X-rays are focused to the same focal position by focusing elements having diffraction characteristics suitable for the wavelengths of the respective X-rays generated by the X-ray generation mechanism.

14 Claims, 13 Drawing Sheets

(51) Int. Cl.
*G21K 7/00* (2006.01)
*H01J 35/28* (2006.01)
*H01J 35/30* (2006.01)

(52) U.S. Cl.
CPC ........... *H01J 35/30* (2013.01); *G01N 2223/204* (2013.01); *G01N 2223/206* (2013.01); *H01J 2235/081* (2013.01); *H01J 2235/086* (2013.01); *H01J 2235/163* (2013.01)

(56) References Cited

U.S. PATENT DOCUMENTS

| | | | | |
|---|---|---|---|---|
| 5,444,242 | A | * | 8/1995 | Larson et al. ................. 250/305 |
| 5,790,628 | A | * | 8/1998 | Ishida .............................. 378/83 |
| 2005/0185764 | A1 | | 8/2005 | Katayama |
| 2007/0010973 | A1 | * | 1/2007 | deCecco et al. ............. 702/189 |

FOREIGN PATENT DOCUMENTS

| | | | |
|---|---|---|---|
| JP | 11-281597 | * | 10/1999 |
| JP | 11-281597 | A | 10/1999 |
| JP | 2001-133421 | A | 5/2001 |
| JP | 2001-351551 | A | 12/2001 |
| JP | 2002-228609 | A | 8/2002 |
| JP | 2005-216578 | A | 8/2005 |
| JP | 2009-500642 | A | 1/2009 |

OTHER PUBLICATIONS

Bearden, J.A. "X-Ray Wavelengths" *Reviews of Modern Physics*, Jan. 1967, 39(1):78-124.
OURSTEX Corporation "X-ray fluorescence analyzer suitable for trace analysis with high accuracy" http://business.atengineer.com/ourstex/product3.htm.
International Search Report in International Application No. PCT/JP2011/001904, filed Mar. 30, 2011.

* cited by examiner

X-RAY IRRADIATION DEVICE AND ANALYSIS DEVICE

CROSS-REFERENCE TO RELATED APPLICATIONS

This application is the U.S. national stage application of International Patent Application No. PCT/JP2011/001904, filed Mar. 30, 2011, which claims priority to Japanese Patent Application No. 2010-080669, filed Mar. 31, 2010, the disclosures of each of which are incorporated herein by reference in their entirety.

TECHNICAL FIELD

The present invention relates to an X-ray irradiation device that focuses X-rays emitted from an X-ray generation mechanism to a predetermined focal position by a focusing mechanism and to an analysis device provided with the X-ray irradiation device.

BACKGROUND ART

X-ray photoelectron spectroscopy (XPS) is known as one of surface analysis methods.

The XPS can acquire information on elements existing in a sample and on a chemical-bonding state by analyzing kinetic energy of photoelectrons that are emitted from a surface of the sample by x-ray irradiation. For example, Patent Document 1 and Non-Patent Document 1 each describe a photoelectron spectroscopy device that includes an electron gun for generating a focused electron beam, an anode for generating X-rays by incidence of the focused electron beam, a focusing means for focusing the X-rays generated in the anode to the surface of a sample, and an analyzer means for analyzing energy of photoelectrons that are emitted from the surface of the sample by X-ray irradiation.

In this type of conventional X-ray analysis device, it has been desired to irradiate X-rays having appropriate energy depending on a sample or the purpose of analysis. For example, Patent Document 2 and Non-Patent Document 2 describe an X-ray spectroscopy device and an X-ray analysis device, including a spectrometer means capable of selecting a plurality of X-rays having different energy in a single device, but it has been considered impossible that a single device adjusts the energy in a wide range and focuses X-rays to the surface of the sample.

Further, it is theoretically known that a non-destructive analysis in a depth direction can be performed by an analysis of spectra of photoelectrons having different take-off angles, depending on the energy of the X-rays. In the current X-ray analysis device, however, the depth of detection is limited to no more than about several nm because photoelectrons are scattered in the sample. For that reason, this theory has been considered to be irrealizable.

Patent Document 1: Japanese Patent Application Laid-open No. Hei 7-325052
Patent Document 2: Japanese Patent Application Laid-open No. 2001-133421
Non-Patent Document 1: Masaaki Kobata et al., "Development of the Hard-X-ray Angle Resolved X-ray Photoemission Spectrometer for Laboratory Use", ANALYTICAL SCIENCES FEBRUARY 2010, VOL. 26, pp. 227-232 (2010)
Non-Patent Document 2: X-ray fluorescence analysis device with high count rate and high resolution (OURSTEX Corporation), http://business.atengineer.com/ourstex/product3.htm
Non-Patent Document 3: J. A. Berden: "X-Ray Wavelengths", Review of Modern Physics, Vol. 39, No. 1, pp. 78-124 (1967)

DISCLOSURE OF THE INVENTION

Problem to be Solved by the Invention

In view of the circumstances as described above, it is an object of the present invention to provide an X-ray irradiation device capable of adjusting the energy of X-rays in a wide range and an analysis device using the X-ray irradiation device.

Means for Solving the Problem

An X-ray irradiation device of Invention 1 is an X-ray irradiation device that focuses X-rays emitted from an X-ray generation mechanism to a predetermined focal position by a focusing mechanism, the X-ray irradiation device being characterized in that: the X-ray generation mechanism has a structure which generates a plurality of X-rays having different wavelengths; and the focusing mechanism has a structure in which the plurality X-rays are focused to the same focal position by focusing elements having diffraction characteristics suitable for the wavelengths of the respective X-rays generated by the X-ray generation mechanism.

Invention 2 is characterized in that, in the X-ray irradiation device of Invention 1, the focusing elements are each an X-ray reflecting mirror whose mirror surface having a curvature radius equal to a diameter of a Rowland circle is arranged on the Rowland circle, the Rowland circle including a generation position of the X-rays suitable for the diffraction characteristics thereof and the focal position with those positions as pass points.

Invention 3 is characterized in that, in the X-ray irradiation device of Invention 2, the X-ray reflecting mirror is provided for each of the wavelengths of the generated X-rays, the X-ray reflecting mirror having a position for use that is set at a position deviated from optical paths of X-rays of wavelengths unsuitable for the diffraction characteristics thereof.

Invention 4 is characterized in that, in the X-ray irradiation device of Invention 2, the X-ray reflecting mirror is provided for each of the wavelengths of the generated X-rays, and the X-ray reflecting mirror whose position for use is set at a position overlapping optical paths of X-rays of wavelengths unsuitable for the diffraction characteristics thereof is provided with a retracting structure that retracts the X-ray reflecting mirror to a position deviated from the optical paths when the X-ray reflecting mirror is not used.

Invention 5 is characterized in that, in any one of the X-ray irradiation devices of Inventions 1 to 4, the X-ray generation mechanism includes an electron gun that emits a constant level of electron beam, a plurality of X-ray sources that generate X-rays having different wavelengths by irradiation with the electron beam, and a wavelength selecting structure that selects the X-ray sources to be irradiated with the electron beam and selects wavelengths of the generated X-rays.

An analysis device of Invention 6 includes the X-ray irradiation device according to any one of Inventions 1 to 5, the analysis device being characterized in that the X-ray irradiation device has a focal position that is set as a position where the sample is placed.

Invention 7 is characterized in that, in the analysis device of Invention 6, the analyzer is configured to detect kinetic energy of photoelectrons emitted from the sample.

Effect of the Invention

Based on the finding that the use of the focusing elements having diffraction characteristics suitable for the wavelength of the X-rays allows the energy of the X-rays and their wavelengths to have a close relationship and allows the energy to be given to a sample at high efficiency, Inventions 1 and 2 each include not only the X-ray generation mechanism that generates a plurality of types of X-rays having different wavelengths but also the focusing mechanism provided with diffraction characteristics suitable for the respective wavelengths of the X-rays. Accordingly, the focal position is irradiated with the X-rays without the energy thereof being attenuated. Further, all the X-rays having different wavelengths are provided with the same focal position so that it becomes unnecessary to change a sample position also by the adjustment of the wavelengths.

This allows an analysis result of the surface and that of the depth direction to be coupled to each other on the same coordinates, to thereby obtain a three-dimensional analysis result.

Inventions 3 and 4 relate to the securement of an optical path space, which is generated when the X-rays having different wavelengths as described above are used.

In Invention 3, in the case where the optical path is mainly directed in a vertical direction, the focusing mechanism is expanded in a horizontal direction by the number of different X-rays, but it becomes unnecessary to make an operation as in Invention 4.

On the other hand, in Invention 4, a compact focusing mechanism with little expansion to the horizontal direction can be obtained, but it becomes necessary to make an operation of moving the focusing elements when the wavelengths are changed.

However, since this operation can be made while changing the wavelengths under automatic control, in actuality it is possible to solve the inconvenience involved in the operation.

Invention 5 indicates a specific good example for changing the wavelengths of the X-rays.

In Invention 5, using the plurality of X-ray sources that generate X-rays having different wavelengths by excitation due to the electron beam, the wavelengths of the X-rays can be set by the X-ray sources to be irradiated with the electron beam. With this operation, the wavelengths of the X-rays can be dynamically changed and can be widely applied depending on the difference in material between samples, the difference in purpose between analyses, and the like.

Inventions 6 and 7 are analysis devices that effectively maximize effects of the X-ray irradiation devices of the present invention. The analysis devices have advantages of the X-ray irradiation devices described above and can additionally obtain analysis results of both the surface and the depth in association with each other, to thereby obtain a three-dimensional X-rays analysis result.

BEST MODE FOR CARRYING OUT THE INVENTION

Figure 1:
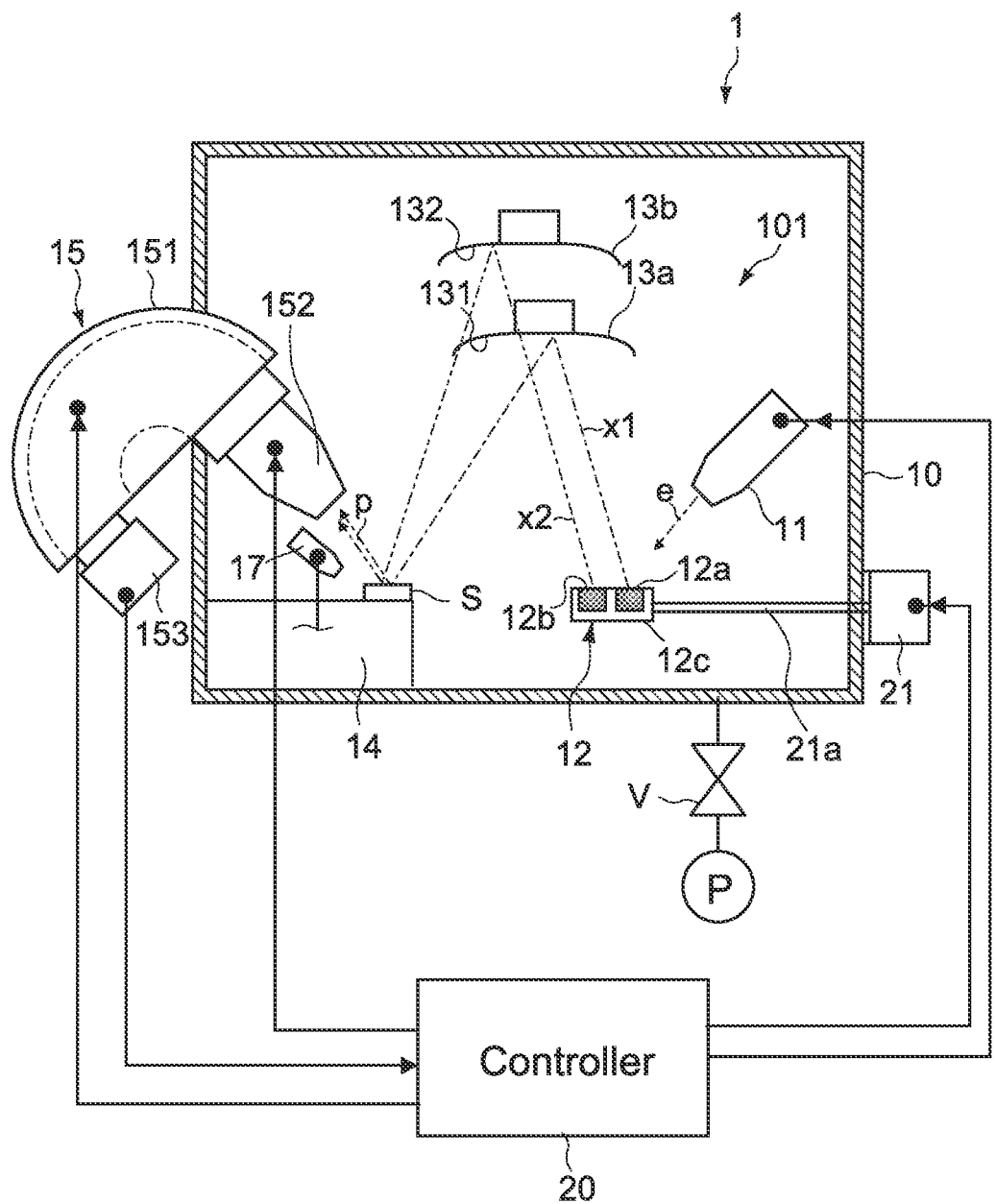
FIG. 1 A structural diagram schematically showing an analysis device according to Example 1.

An X-ray irradiation device according to the present invention is an X-ray irradiation device that focuses X-rays emitted from an X-ray generation mechanism to a predetermined focal position by a focusing mechanism. The X-ray generation mechanism has a structure which generates a plurality of X-rays having different wavelengths. The focusing mechanism has a structure in which the plurality of X-rays are focused to the same focal position by focusing elements having diffraction characteristics suitable for the wavelengths of the respective X-rays generated by the X-ray generation mechanism.

In Examples, exemplified as the focusing element is an X-ray reflecting mirror whose mirror surface having a curvature radius equal to a diameter of a Rowland circle is arranged on the Rowland circle, the Rowland circle including a generation position of the X-rays suitable for the diffraction characteristics thereof and the focal position with those positions as pass points. However, the present invention is not limited thereto. Any focusing element may be used as long as it has the diffraction characteristics suitable for the wavelengths of the X-rays generated by the X-ray generation mechanism.

It should be noted that the suitability of the diffraction characteristics means that a highly accurate analysis with high energy resolution is realized by allowing the X-rays to be monochromated and removing a continuous spectrum part of the X-rays.

Further, since some focusing elements, even if they are similar to one other as shown in Table 1, have diffraction characteristics suitable for the X-rays having a plurality of wavelengths, the number of wavelengths of X-rays to be generated and the number of focusing elements do not necessarily correspond to each other. Depending on circumstances, the focusing mechanism can be structured by one focusing element.

Exemplified as an example of the X-ray generation mechanism is one including an electron gun that emits a constant level of electron beam, a plurality of X-ray sources that generate X-rays having different wavelengths by irradiation with the electron beam, and a wavelength selecting structure that selects the X-ray sources to be irradiated with the electron beam and selects wavelengths of the generated X-rays.

Furthermore, as the X-ray sources, ones shown in Table 1 are generally known. Examples herein are premised on that a plurality of X-ray sources shown in Table 1 are selected to be used.

TABLE 1

| X-ray source | X-ray name | Wave-length Å | Energy keV | Rowland circle Diameter (mm) | Reflecting mirror having suitable wavelength characteristics |
|---|---|---|---|---|---|
| Al | AlKα | 8.34 | 1.49 | 200 | Curved quartz crystal |
| Zr | ZrLα$_1$ | 6.07 | 2.04 | 162 | Curved Si crystal |
| Ag | AgLα$_1$ | 4.15 | 2.98 | 184 | Curved quartz crystal |
| Ti | TiKα$_1$ | 2.75 | 4.51 | 170 | Curved Ge crystal |
| Cr | CrKα$_1$ | 2.29 | 5.41 | 300 | Curved Ge crystal |
|    | CrKβ$_{1,3}$ | 2.08 | 5.95 | 200 | Curved quartz crystal |
| Cu | CuKα$_1$ | 1.54 | 8.05 | 459 | Curved LiF crystal |

In addition to Examples below, X-ray sources that generate X-rays having different wavelengths by an incident voltage of the electron beam may be used. As an anode material of the X-ray sources, not only a plurality of pure substance anodes but also a single alloy anode such as a CuAl alloy of 80 at % Al/20 at % may be prepared. In this case, AlKα-rays can be generated when the incident voltage of the electron beam is less than 9 kV, and CuKα-rays and AlKα-rays can be generated when the incident voltage of the electron beam exceeds 9 kV. In the latter case, only the CuKα-rays can be selected by use of focusing elements having diffraction characteristics suitable for the CuKα-rays.

This is because the energy of the AlKα-rays and that of the CuKα-rays are about 1.49 keV and 8.05 keV, respectively, and the CuKα-rays are generated only when the incident voltage of the electron beam is the binding energy of CuK-shell electron (8.98 keV) or more, that is, 9 kV or more. Accordingly, the generation of the AlKα-rays or the generation of the CuKα-rays and AlKα-rays can be selected with the incident voltage of the electron beam, 9 kV, being set to a threshold value. Further, for the plurality of anode materials used herein, it is desirable to select a combination of materials whose energy of X-rays are largely different from each other, such as Al and Cu.

For the reasons described above, by preparing a single alloy anode and selectively generating KαX-rays in accordance with the incident voltage of the electron beam, an amount of movement of the electron gun for irradiating an appropriate position of the anode material with the electron beam and the number of anode materials can be reduced as much as possible.

Furthermore, to obtain an appropriate intensity of X-rays, the incident voltage of the electron beam is desirably five times or more the energy of the X-rays generated from the respective anode materials.

It should be noted that the relationship between a dispersive crystal (type, plane index of crystal surface, and grid constant) having diffraction characteristics suitable for wavelengths of various types of characteristic X-rays and a diffraction angle (2θ) is known by the description of Non-Patent Document 3, and this known finding can be used also in the present invention.

In Examples below, exemplified as an analysis device is one that detects kinetic energy of photoelectrons emitted from a sample by irradiation of the sample with the X-rays, but in addition thereto, Examples below can be applied to a surface analysis device with X-rays being used as an excitation line, for example, to an X-ray fluorescence analysis (XRF) device or a photo-emission electron microscope (PEEM).

Hereinafter, an embodiment of the present invention will be described with reference to the drawings.

Example 1

Figure 2:
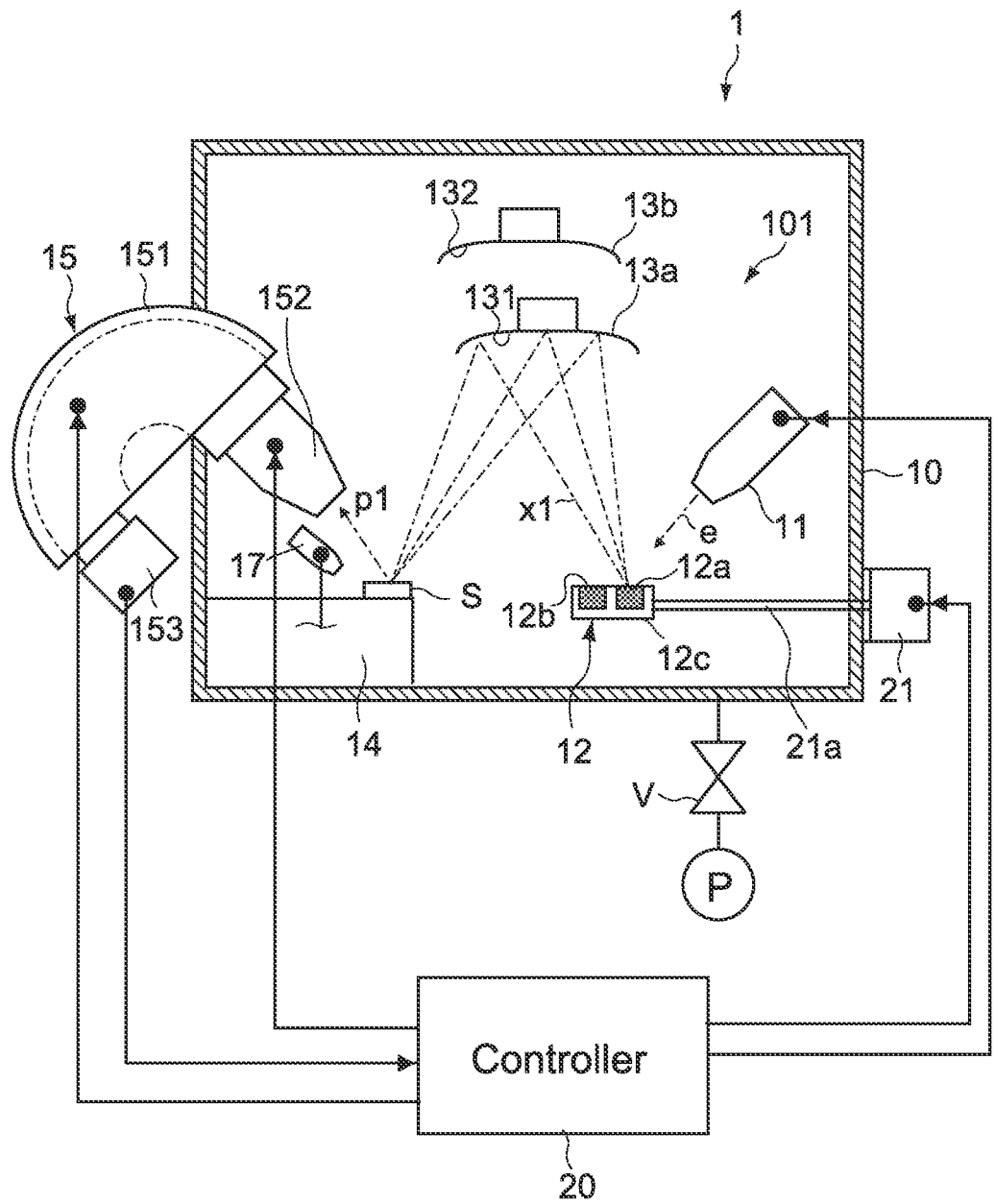
FIG. 2 A structural diagram of the analysis device of FIG. 1, schematically showing an operation example of the device.
Figure 3:
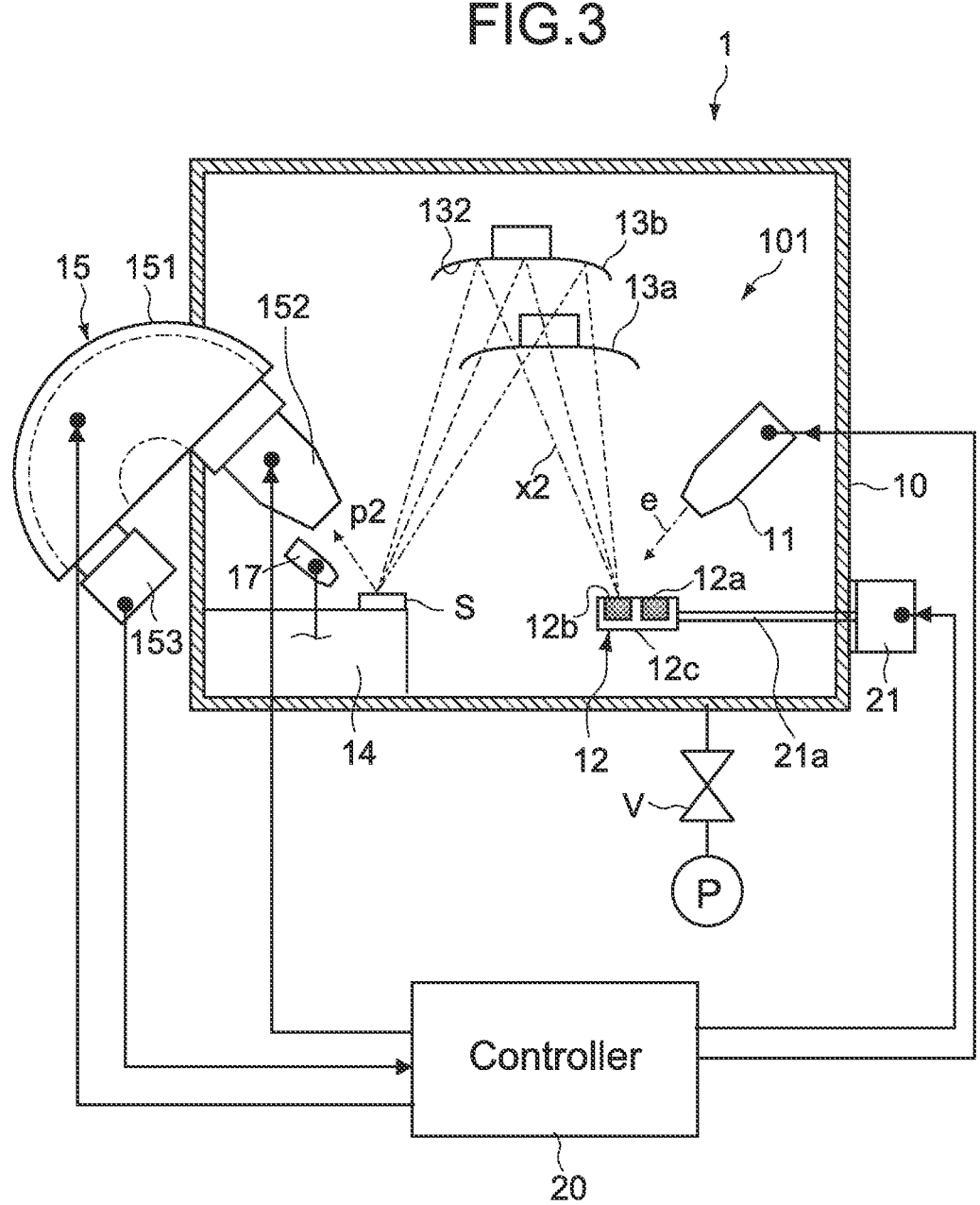
FIG. 3 A structural diagram of the analysis device of FIG. 1, schematically showing another operation example of the device.

FIG. 1 is a structural diagram schematically showing an analysis device according to this example. In this example, an X-ray photoelectron spectroscopy device (XPS device) is exemplified as an analysis device. FIGS. 2 and 3 are schematic diagrams of the same in FIG. 1, showing an operation example of the analysis device.

An analysis device 1 of this example includes a chamber 10, an X-ray irradiation device 101, a stage 14, an analyzer 15, and a controller 20.

The chamber 10 is connected to a vacuum pump P via a vacuum valve V and can be exhausted to a predetermined pressure (for example, $10^{-7}$-Pa range) and kept.

The X-ray irradiation device 101 includes an electron gun 11, an anode 12, a first focusing element 13a and a second focusing element 13b.

The electron gun 11 is disposed inside the chamber 10 and irradiates the anode 12 with an electron beam (e). The electron gun 11 includes an electron source that generates electrons and an electron lens capable of focusing the generated electrons to be adjusted to have a predetermined bean diameter. The electron source may be a hot cathode or a cold cathode. The electron lens may be of an electric-field type or a magnetic-field type. Further, the electron gun 11 includes a deflector capable of deflecting the electron beam. The operations of generating, focusing, deflecting the electron beam by the electron gun 11 are controlled by the controller 20.

The anode 12 includes a first anode element 12a, a second anode element 12b, and a support body 12c that supports the first and second anode elements 12a and 12b. The first and second anode elements 12a and 12b are formed of different types of metal materials and each function as an X-ray source that generates X-rays (characteristic X-rays) having a unique wavelength by being irradiated with an electron beam. The support body 12c is formed of a metal material excellent in thermal conductivity, such as silver (Ag) or copper (Cu). Inside the support body 12c, a cooling channel through which cooling water circulates is formed.

In this example, Al is used as the first anode element 12a, and Cr is used as the second anode element 12b. The first anode element 12a generates AlKα-rays (wavelength: 8.34 Å, energy: 1.49 keV) as first X-rays (x1) by being irradiated with the electron beam from the electron gun 11. The second anode element 12b generates CrKα-rays (wavelength: 2.29 Å, energy: 5.41 keV) as second X-rays (x2) by being irradiated with the electron beam from the electron gun 11. The electron gun 11 has a state where the first anode element 12a is irradiated with the electron beam therefrom (first state) and a state where the second anode element 12b is irradiated with the electron beam therefrom (second state). The condition of irradiation with the electron beam is independently controlled in the respective states.

The support body 12c is structured such that a relative position with respect to the electron gun 11 is variable by the first movement mechanism 21. The first movement mechanism 21 is disposed on the outer surface of the chamber 10 and includes a drive rod 21a that passes through the chamber 10 via a vacuum seal (not shown). The drive rod 21a is coupled to the support body 12c. The first movement mechanism 21 is constituted of a cylinder device, a ball screw unit, a servomotor, or the like and moves the support body 12c in a horizontal direction by extending and retracting the drive rod 21a. The operation of the first movement mechanism 21 is controlled by the controller 20.

In this example, the irradiation area of the electron beam by the electron gun 11 is fixed to a certain range, and the support body 12c is moved such that the first anode element 12a or the second anode element 12b is located in the irradiation area of the electron beam. Specifically, as shown in FIG. 2, when the first X-rays generate, the first movement mechanism 21 moves the support body 12c to a position where the first anode element 12a is irradiated with the electron beam (first position). Further, as shown in FIG. 3, when the second X-rays generate, the first movement mechanism 21 moves the support body 12c to a position where the second anode element 12b is irradiated with the electron beam (second position).

It should be noted that though not shown in the figures, the support body 12c is moved along a base provided in the chamber 10. Further, the first movement mechanism 21 is not limited to the structure in which the support body 12c is moved by the operation of expanding and retracting the drive rod 21a. For example, the support body 12c may be structured to be movable by a gear mechanism disposed inside the base described above. Those electron gun 11, anode 12, and movement mechanism 21 form an "X-ray generation mechanism" according to the present invention.

The first and second focusing elements 13a and 13b form a "focusing mechanism" according to the present invention and are each arranged inside the chamber 10. The first focusing element 13a is for focusing the first X-rays (Al Kα line) generated in the first anode element 12a to a surface of a sample S on the stage 14. On the other hand, the second focusing element 13b is for focusing the second X-rays (Cr Kα line) generated in the second anode element 12b to the surface of the sample S on the stage 14.

The first focusing element 13a includes a first mirror surface 131 that the first X-rays (Al Kα line) enter, and the second focusing element 13b includes a second mirror surface 132 that the second X-rays (Cr Kα line) enter. Those mirror surfaces 131 and 132 each form a concave-surface reflecting mirror that focuses the X-rays to minute regions on the surface of the sample S by reflecting toward the sample S the X-rays emitted from the anode elements 12a and 12b. Accordingly, the surface analysis of the fine regions of the sample S can be performed. It should be noted that a spot diameter of the X-rays on the sample S depends on a beam diameter of the electron beam output from the electron gun 11, the accuracy of a dispersive crystal that constitutes a focusing element, and the like and is set to, for example, a diameter of 5 μm to 200 μm.

Further, the focusing elements 13a and 13b are each constituted of a dispersive crystal (monochromator) that monochromates the incident X-rays. The dispersive crystal has a function of selectively reflecting only X-rays having a predetermined wavelength that satisfy the Bragg reflection condition. In this example, the focusing elements 13a and 13b each remove a continuous spectrum part from the incident X-rays and selectively reflect only desired characteristic X-rays (Al Kα line, Cr Kα line). Accordingly, the highly-accurate surface analysis with high energy resolution can be realized in the analyzer 15.

As the dispersive crystal that constitutes the focusing elements 13a and 13b, a material that has a grid constant corresponding to an X-ray wavelength to be a target is used. In this example, a crystal is used for the first focusing element 13a that focuses the first X-rays (Al Kα line). Further, a Ge (germanium) crystal is used for the second focusing element 13b that focuses the second X-rays (Cr Kα line).

The anode elements 12a and 12b and X-rays to be excited therefrom can be appropriately selected in a range described in Table 1 or a range exceeding the range described in Table 1. The focusing elements 13a and 13b can be appropriately selected in accordance with the wavelength of the selected X-rays. The focusing elements 13a and 13b are not limited to the case of being formed of the dispersive crystal described above and may be formed of a diffraction grating or a multi-layered optical film.

The first and second focusing elements 13a and 13b are arranged in the vacuum chamber 10 so as to each have the same focal position. Accordingly, the same spot of the sample S can be irradiated with the X-rays having different wavelengths. To obtain such a function, the mirror surfaces 131 and 132 of the focusing elements are arranged on the circumferences of a plurality of different Rowland circles that each pass through the anode 12 and the focal position described above.

Figure 4:
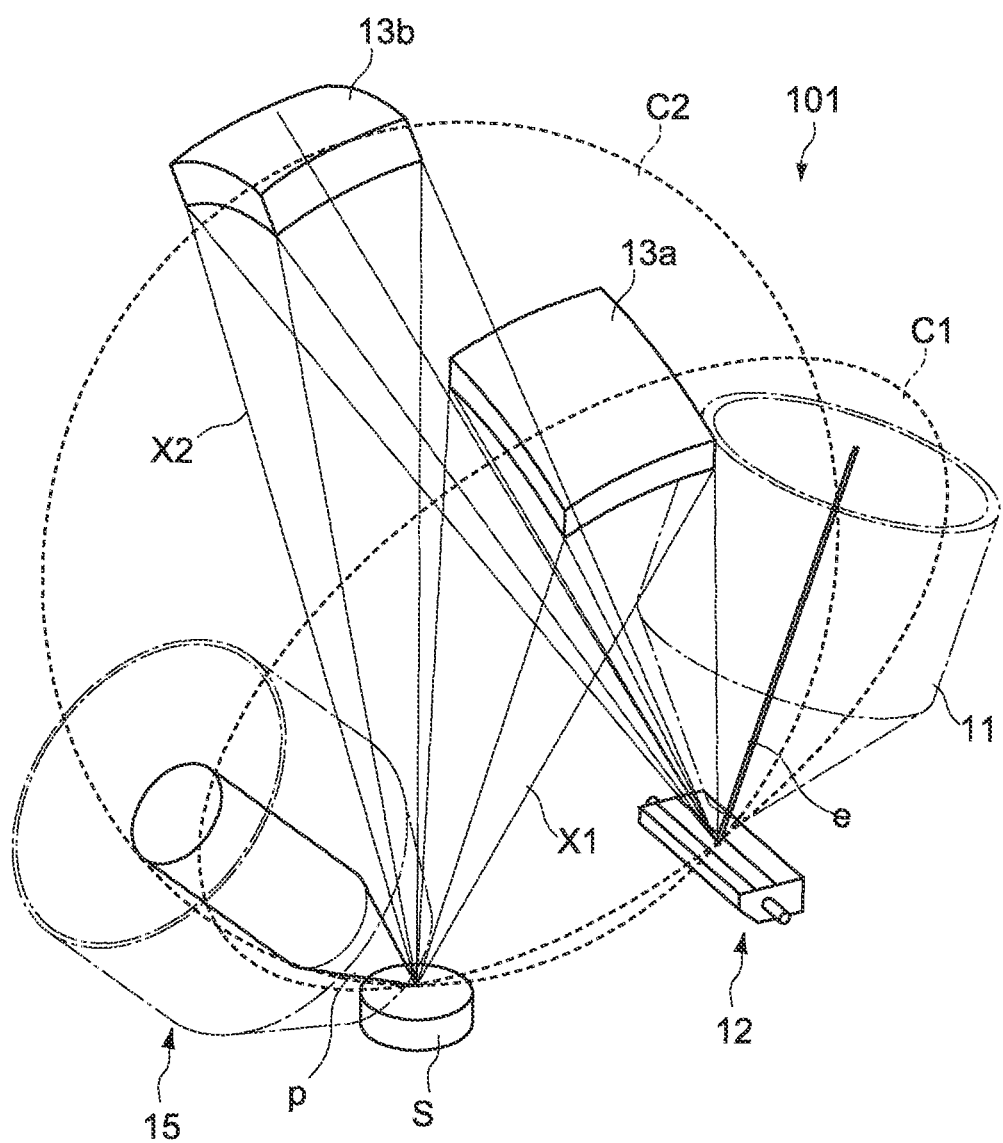
FIG. 4 A schematic perspective diagram of an X-ray irradiation device used in the analysis device of FIG. 1.

FIG. 4 is a schematic perspective diagram of the X-ray irradiation device 101, for explaining a relative position relationship among the anode 12, the sample S (stage 14), and the first and second focusing elements 13a and 13b. As shown in FIG. 4, the first focusing element 13a has the mirror surface 131 having a curvature that is equal to twice the diameter of a Rowland circle (first Rowland circle) C1 with a generation position of the X-rays suitable for the diffraction characteristics thereof and the focal position on the sample S as pass points, and the mirror surface 131 is arranged on the first Rowland circle C1. On the other hand, the second focusing element 13b has the mirror surface 132 having a curvature radius that is equal to the diameter of a Rowland circle (second Rowland circle) C2 with a generation position of the X-rays suitable for the diffraction characteristics thereof and the focal position on the sample S as pass points, and the mirror surface 132 is arranged on the second Rowland circle C2. Accordingly, the X-rays having the respective wavelengths can be efficiently focused to the focal position. Further, by forming the focusing surfaces 131 and 132 into a spheroid surface shape, an aberration of the X-rays at the focal position can be reduced. The mirror surfaces 131 and 132 of the focusing elements 13a and 13b may have a toroidal surface shape, though the aberration is larger than that of the spheroid surface.

The first and second focusing elements 13a and 13b are arranged at positions where the X-rays output from the anode elements 12a and 12b enter the mirror surfaces 131 and 132 of the respective focusing elements at an incident angle close to a perpendicular angle. Thus, a solid angle or e'tendue is largely reduced, and high-flux X-rays focused to the focal position on the sample S can be achieved.

Next, the stage 14 is structured as a support stage that supports the sample S with its surface facing up. The stage 14 may include a transfer mechanism for transferring the sample S between the inside and the outside of the chamber 10, a ground mechanism for keeping the sample S at an earth potential, and the like.

The analyzer 15 disperses photoelectrons (p) that are emitted from the surface of the sample S on the stage 14, by being irradiated with the X-rays (Al Kα line, Cr Kα line). The analyzer 15 includes an analyzer main body 151 that disperses kinetic energy of the photoelectrons, an input lens 152 that guides the photoelectrons to the analyzer main body 151, and a detector 153 that detects the photoelectrons dispersed by the analyzer main body 151.

The analyzer main body 151 includes a plurality of electrodes for electrostatically dispersing the photoelectrons, and a voltage applied to those electrodes is controlled by the controller 20. The input lens 152 includes a multistage electrode unit, and a voltage to be applied to those electrodes is also controlled by the controller 20. The detector 153 includes, for example, an electron multiplier, and an output thereof is supplied to the controller 20.

The controller 20 is constituted of a computer for example, and controls the operations of the electron gun 11, the first movement mechanism 21, and the analyzer 15. The controller 20 executes the surface analysis of the sample S according to a predetermined algorithm, and displays results of the analysis on a display (not shown) or stores them in a predetermined storage unit.

It should be noted that the analysis device 1 of this example includes an electron irradiation source 17 for charge neutralization of the surface of the sample S. In the case where the surface of the sample S is constituted of an insulation material, the surface may be charged up to be positive due to the emission of the photoelectrons. To prevent this, the electron irradiation source 17 irradiates the sample S with low energy electrons. The operation of the electron irradiation source 17 is controlled by the controller 20.

The analysis device 1 of this example is structured as described above. Next, the operation of the analysis device 1 will be described.

In this example, the surface analysis using the first X-rays (Al Kα line) and the surface analysis using the second X-rays (Cr Kα line) are independently performed.

First, the surface analysis using the first X-rays (Al Kα line) will be explained. FIG. 2 shows a state of the surface analysis of the sample S by use of the first X-rays. By controlling the first movement mechanism 21, the controller 20 moves the support body 12c to a position where the first anode (Al anode) 12a is irradiated with the electron beam (first position).

The electron gun 11 irradiates the electron beam (e) to the first anode element 12a, to thereby generate the first X-rays (x1: Al Kα line) from the first anode element 12a. The first X-rays enter the first focusing element 13a and are then reflected on the mirror surface 131 toward the surface of the sample S on the stage 14. Since the first focusing element 13a has the concave surface shape described above and is formed of a predetermined dispersive crystal, the first X-rays reflected on the focusing element 13a are monochromated and focused onto the surface of the sample S.

By being irradiated with the first X-rays, the sample S emits photoelectrons (p1) excited by the energy of the first X-rays. The emitted photoelectrons are guided to the analyzer main body 151 via the input lens 152, and after being dispersed, detected with the detector 153. The controller 20 sweeps the input voltage applied to the analyzer main body 151 and the input lens 152 within a predetermined range, to thereby acquire an energy distribution of a photoelectron intensity.

Next, the surface analysis using the second X-rays (Cr Kα line) will be explained. FIG. 3 shows a state of the surface analysis of the sample S by use of the second X-rays. By controlling the first movement mechanism 21, the controller 20 moves the support body 12c to a position where the second anode (Cr anode) 12b is irradiated with the electron beam (second position).

The electron gun 11 irradiates the electron beam (e) to the second anode element 12b, to thereby generate the second X-rays (x2: CrKα-rays) from the second anode element 12b. The second X-rays enter the second focusing element 13b and are then reflected on the mirror surface 132 toward the surface of the sample S on the stage 14. Since the second focusing element 13b has the concave surface shape described above and is formed of a predetermined dispersive crystal, the second X-rays reflected on the refocusing element 13b are monochromated and focused onto the surface of the sample S.

By being irradiated with the second X-rays, the sample S emits photoelectrons (p2) excited by the energy of the second X-rays. The emitted photoelectrons are guided to the analyzer main body 151 via the input lens 152, and after being dispersed, detected with the detector 153. The controller 20 sweeps the input voltage applied to the analyzer main body 151 and the input lens 152 within a predetermined range, to thereby acquire an energy distribution of a photoelectron intensity.

As described above, in this example, the surface analysis is performed on the same position of the sample S by using the first and second X-rays having different wavelengths. Since the X-rays having the respective wavelengths have each different energy, the kinetic energy of the photoelectrons emitted from the surface of the sample S differs depending on the types of the X-rays. Therefore, for example, by obtaining a difference between the energy distribution of the photoelectron intensity acquired by using the first X-rays and the energy distribution of the photoelectron intensity acquired by using the second X-rays, information on depth, which cannot be acquired by using the first X-rays, can be acquired.

Figure 5:
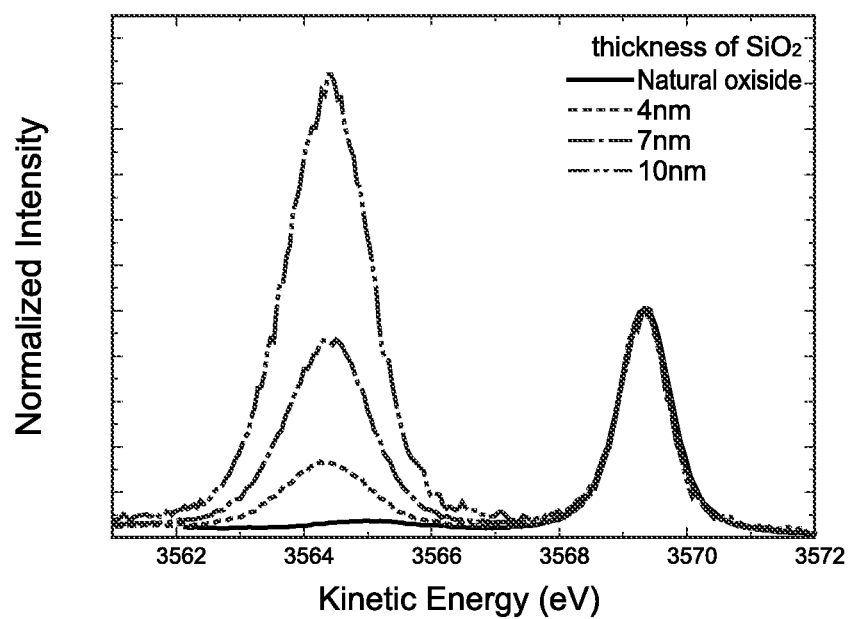
FIG. 5 A diagram showing an example of photoelectron spectra acquired in Example 1.

FIG. 5 shows photoelectron spectra obtained by irradiating a Si-substrate with the Cr Kα line, the Si-substrate having a surface on which an $SiO_2$ film is formed in a thickness of 25 nm. A peak derived from $SiO_2$ is found around 3564.5 eV, and a peak derived from the Si substrate is found around 3569 eV. Though not shown in the figure, in the case of using Al Kα as a source of rays, a peak derived from the Si substrate as a base material was not found.

As described above, according to this example, the energy of the X-rays can be adjusted in a wide range, and a composition analysis at different depth levels between the first X-rays and the second X-rays or an analysis of a chemical-bonding state can be performed. Accordingly, information on a chemical-bonding state and elements with different depths can be acquired without destroying the surface of the sample S.

Example 2

Figure 6:
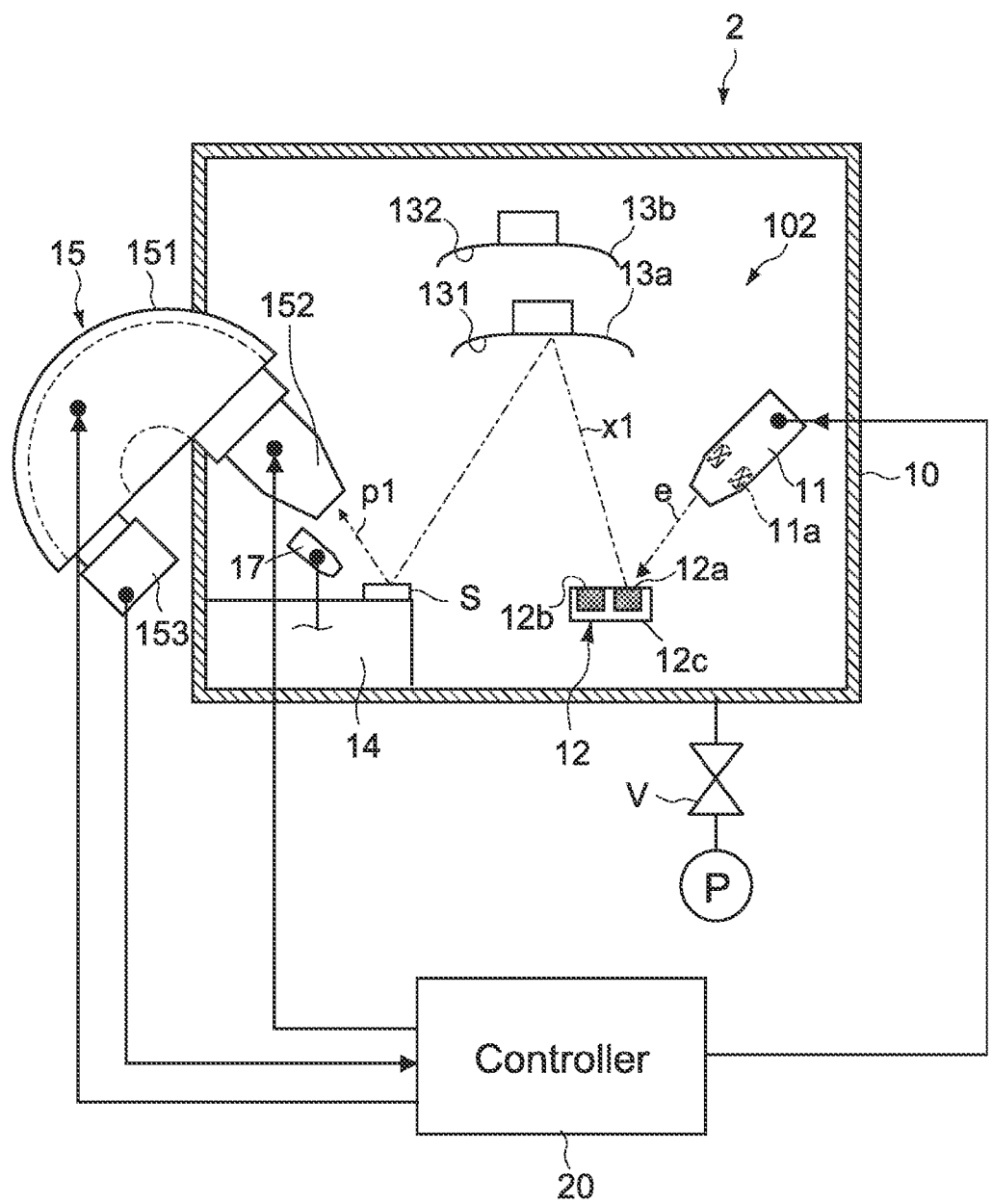
FIG. 6 A structural diagram schematically showing an analysis device according to Example 2.
Figure 7:
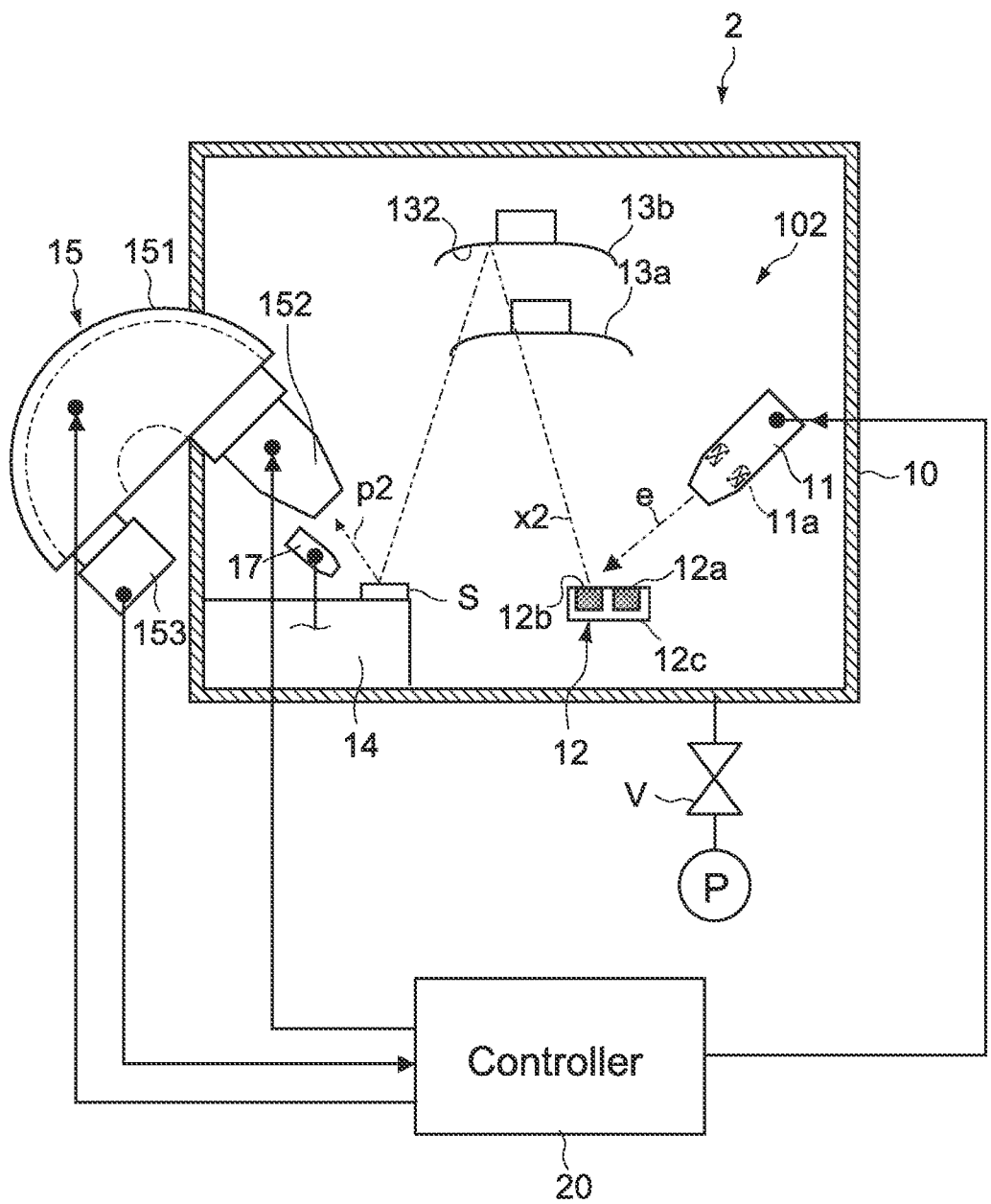
FIG. 7 A structural diagram of the analysis device of FIG. 6, schematically showing an operation example of the device.

FIGS. 6 and 7 show an analysis device according to this example. It should be noted that in the figures, portions corresponding to those in Example 1 described above are denoted by the same reference symbols, and detailed descriptions thereof will be omitted.

In Example 1 described above, by moving the anode 12 relative to the electron gun 11 by the first movement mechanism 21, the state where the first anode element 12a is irradiated with the electron beam (e) and the state where the second anode element 12b is irradiated with the electron beam (e) are switched. In this example, provided is an X-ray irradiation device 102 including an X-ray generation mechanism capable of selectively generating the first X-rays (x1) and the second X-rays (x2) by fixing the position of the anode 12 and switching an irradiation direction of the electron beam (e) by the electron gun 11.

In this example, the electron gun 11 includes a deflector 11a. The deflector 11a is controlled by the controller 20, and a state where the first anode element 12a is irradiated with the electron beam (e) as shown in FIG. 6 and a state where the second anode element 12b is irradiated with the electron beam (e) as shown in FIG. 7 are selectively switched. Accordingly, the surface analysis of the sample S using the first X-rays and the surface analysis of the sample S using the second X-rays can be easily switched by the operation of deflecting the electron beam by the electron gun 11. Here, the controller 20 forms a "wavelength selecting structure" according to the present invention, which selects a wavelength of X-rays to be generated.

According to this example, actions and effects that are the same as those in Example 1 described above can be obtained. In particular, according to this example, since the movement mechanism of the anode 12 is not necessary, the device structure and the control can be simplified.

Example 3

Figure 8:
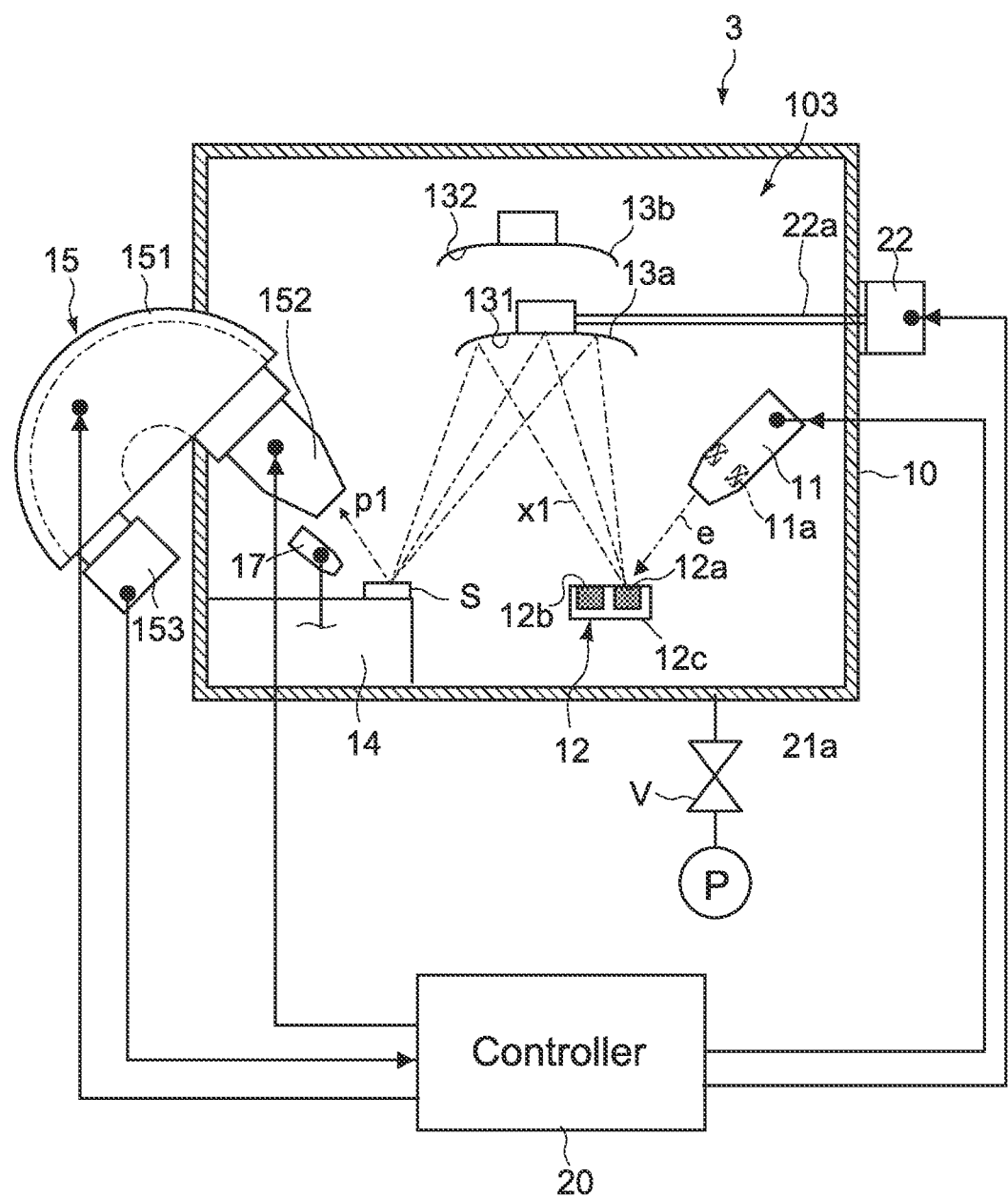
FIG. 8 A structural diagram schematically showing an analysis device according to Example 3.
Figure 9:
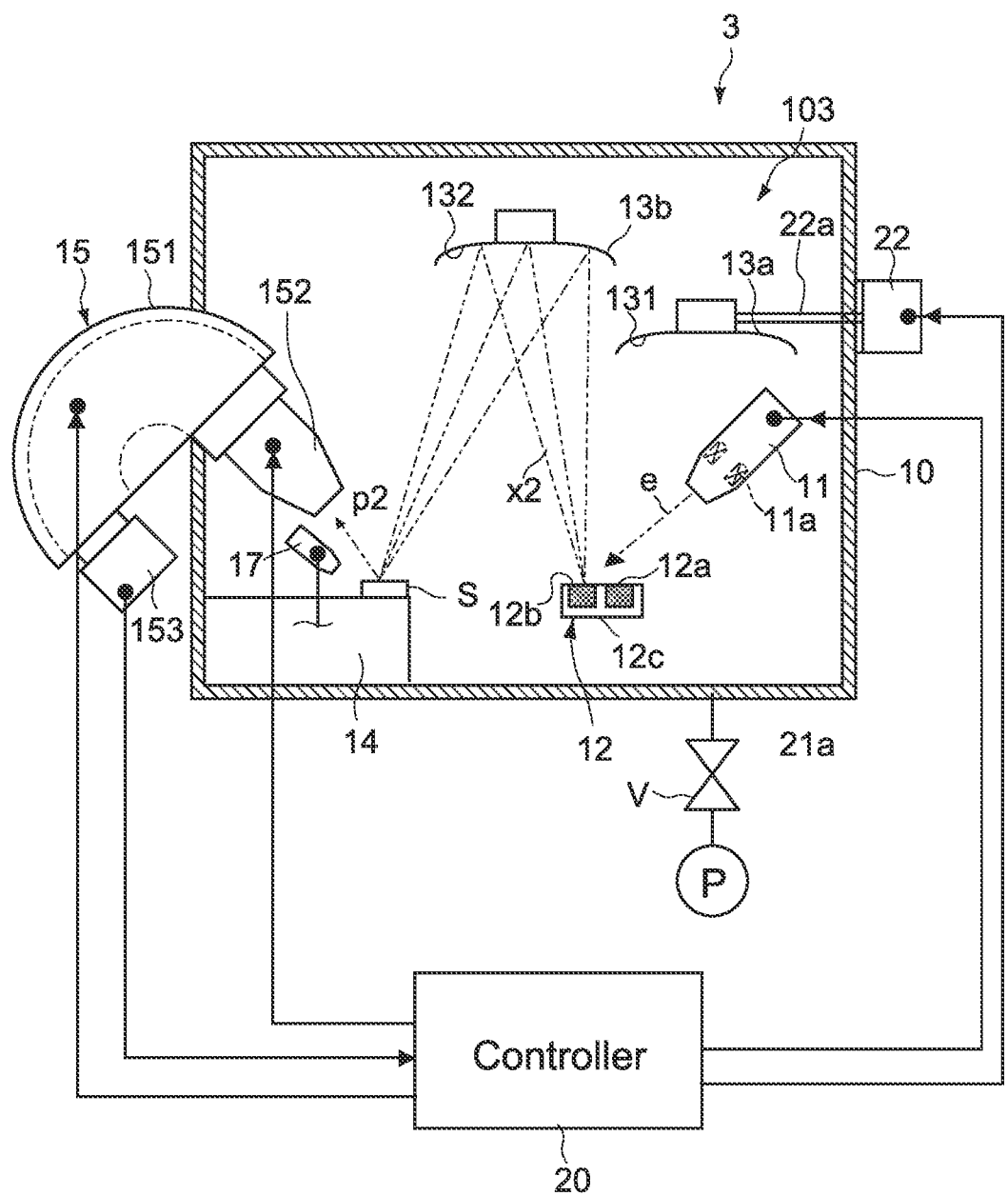
FIG. 9 A structural diagram of the analysis device of FIG. 8, schematically showing an operation example of the device.

FIGS. 8 and 9 show an analysis device according to this example. It should be noted that in the figures, portions corresponding to those in Examples 1 and 2 described above are denoted by the same reference symbols, and detailed descriptions thereof will be omitted.

In Examples described above, the first and second focusing elements 13a and 13b are arranged at the predetermined fixed positions. However, there may be a case where the anode elements 12a and 12b, the sample S, and the focusing elements 13a and 13b cannot be arranged in the geometrically-arranged relationship as described above while actions of focusing the X-rays by the focusing elements 13a and 13b do not interfere with each other, due to the limits on the shape, size, and the like of the chamber 10. Therefore, an analysis device 3 according to this example includes a second movement mechanism 22 for changing a relative relationship between the first focusing element 13a and the second focusing element 13b.

In this example, the first focusing element 13a is arranged at a position closer to the anode 12 than the second focusing element 13b. In this regard, in this example, the first focusing element 13a is moved relative to the second focusing element 13b, to thereby change relative positions between those two focusing elements 13a and 13b. The second movement mechanism 22 forms a "sliding mechanism" according to the present invention. Further, those focusing elements 13a and 13b and second movement mechanism 22 form a "focusing mechanism" according to the present invention, and the focusing mechanism, the electron gun 11, and the anode 12 form an X-ray irradiation device 103 according to this example.

The second movement mechanism 22 is disposed on the outer surface of the chamber 10 and includes a drive rod 22a that passes through the chamber 10 via a vacuum seal (not shown). The drive rod 22a is coupled to the first focusing element 13a. The second movement mechanism 22 is constituted of a cylinder device, a ball screw unit, a servomotor, or the like and moves the first focusing element 13a in a horizontal direction by extending and retracting the drive rod 22a. The operation of the second movement mechanism 22 is controlled by the controller 20.

In this example, the second movement mechanism 22 arranges the first focusing element 13a on the first Rowland circle C1 (FIG. 4) when the first X-rays are generated as shown in FIG. 8. On the other hand, the second movement mechanism 22 horizontally moves the first focusing element 13a to a position where the focusing action of the second X-rays by the second focusing element 13b arranged on the second Rowland circle C2 (FIG. 4) is not inhibited, when the second X-rays are generated as shown in FIG. 9.

Though not shown in the figures, the first focusing element 13a is moved along a guide unit (not shown) disposed inside the chamber 10. Further, the structure of the second movement mechanism 22 is not limited to the one in which the first focusing element 13a is moved by the operation of expanding and retracting the drive rod 22a.

It should be noted that instead of the examples described above, the first focusing element 13a and the second focusing element 13b may be structured to be movable so that the first focusing element 13a is arranged on the first Rowland circle C1 when the first X-rays are generated, and the second focusing element 13b is arranged on the second Rowland circle C2 when the second X-rays are generated.

According to this example as well, actions and effects that are the same as those in Example 1 described above can be obtained. According to this example, since the relative positions between the first and second focusing elements 13a and 13b can be changed, the chamber 10 can be downsized and a degree of freedom of an arrangement layout of constituent members within the chamber 10 can be increased. Further, since the X-ray irradiation device 103 of this example includes the deflector 11a that is provided to the electron gun 11 and is capable of performing the operation of deflecting the electron beam, variations in focal position resulting from a movement error of the first focusing element 13a can be eliminated by changing the position where the anode element 12a is irradiated with the electron beam.

Example 4

Figure 10:
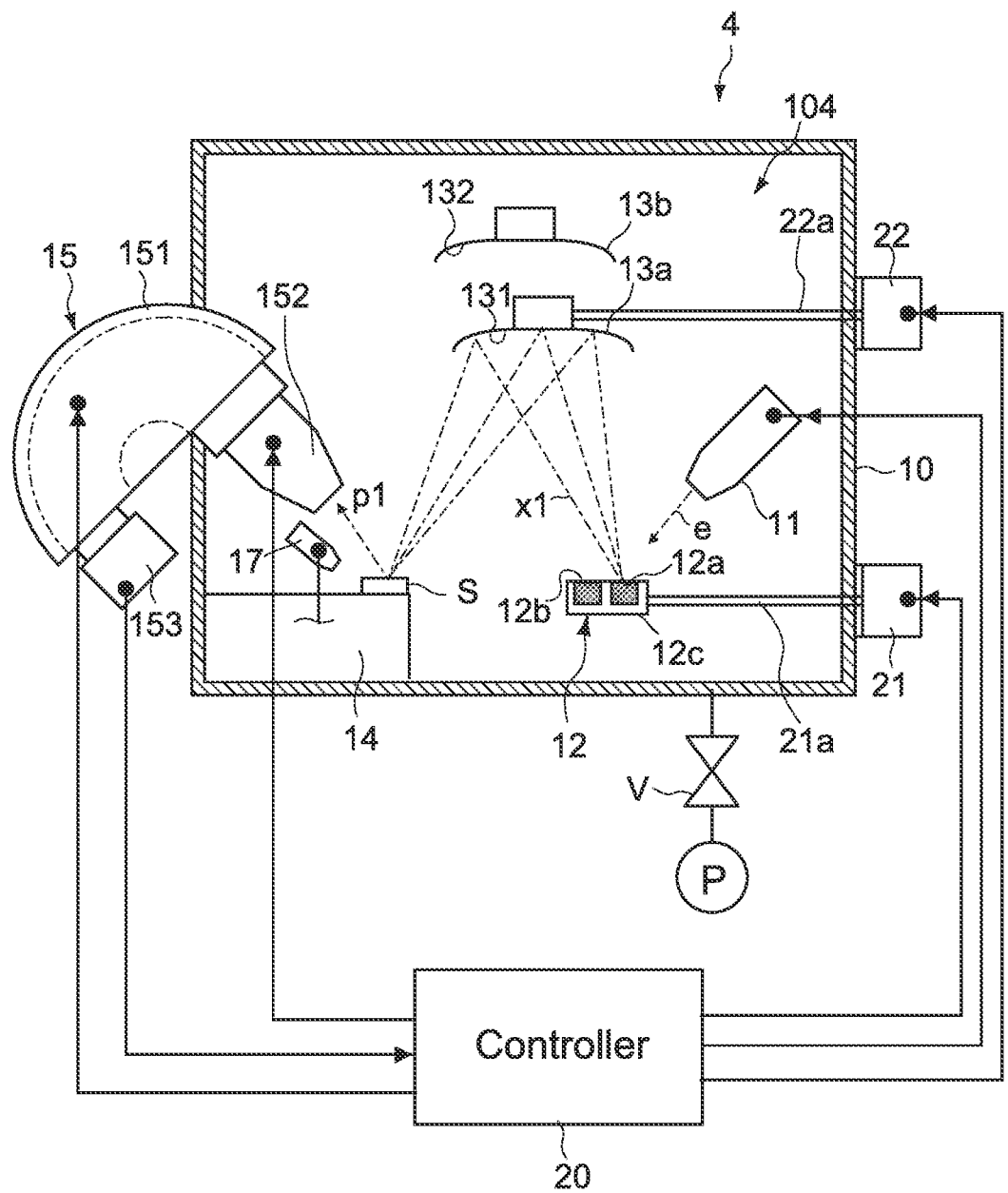
FIG. 10 A structural diagram schematically showing an analysis device according to Example 4.
Figure 11:
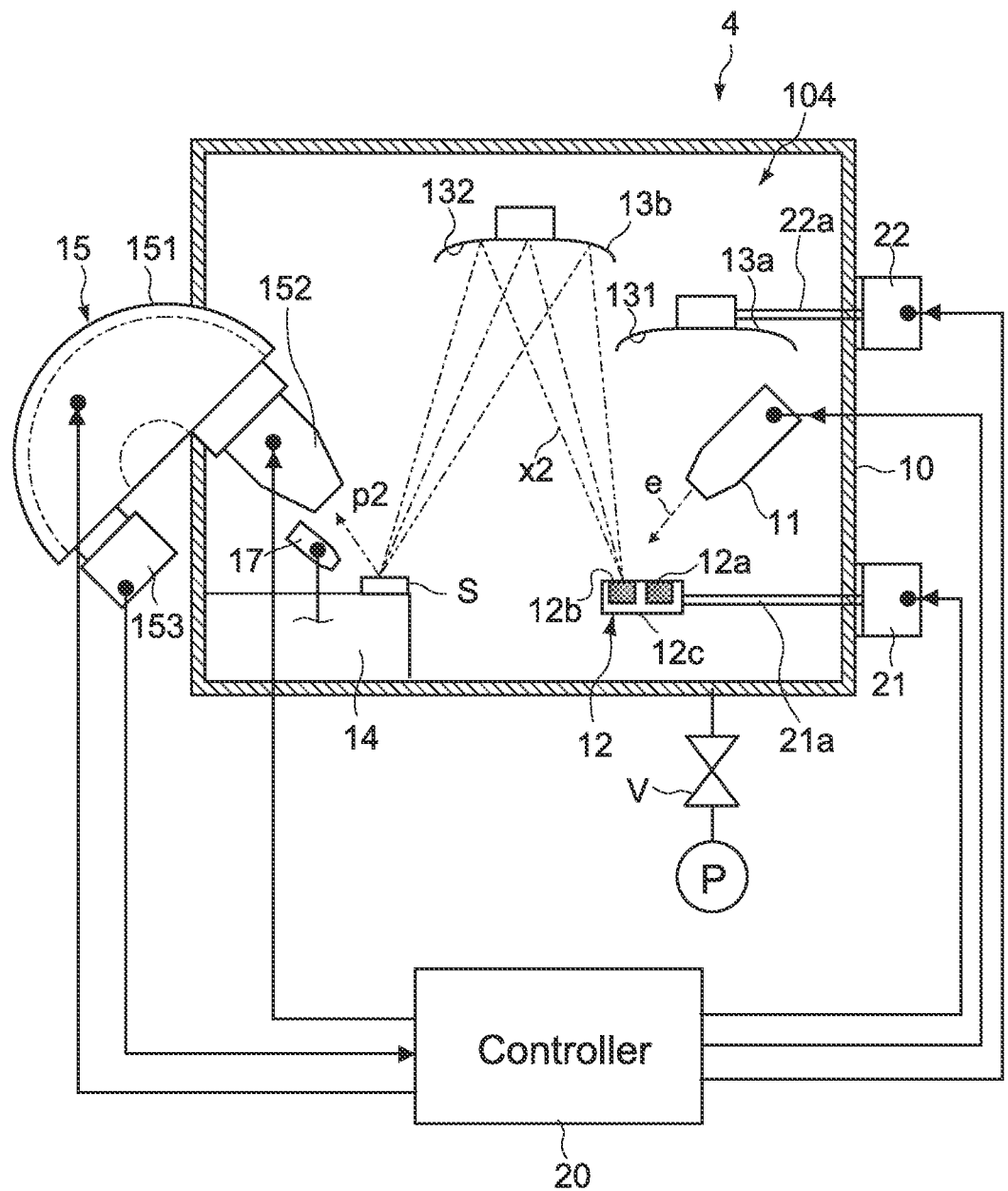
FIG. 11 A structural diagram of the analysis device of FIG. 10, schematically showing an operation example of the device.

FIGS. 10 and 11 show an analysis device according to this example. It should be noted that in the figures, portions corresponding to those in Examples 1 and 2 described above are denoted by the same reference symbols, and detailed descriptions thereof will be omitted.

An analysis device 4 according to this example relates to a combination of Examples 1 and 3 described above and includes an X-ray irradiation device 104 that includes the first movement mechanism 21 capable of moving the anode 12 relative to the electron gun 11, and the second movement mechanism 22 capable of changing relative positions between the first and second focusing elements 13a and 13b.

FIG. 10 shows a state of a surface analysis of the sample S by use of the first X-rays. By controlling the first movement mechanism 21, the controller 20 moves the support body 12c to a position where the first anode (Al anode) 12a is irradiated with the electron beam (first position). Further, by controlling the second movement mechanism 22, the controller 20 arranges the first focusing element 13a (mirror surface 131) on the first Rowland circle C1 (FIG. 4). Accordingly, the surface analysis of the sample S using the first X-rays is performed.

FIG. 11 shows a state of a surface analysis of the sample S by use of the second X-rays. By controlling the first movement mechanism 21, the controller 20 moves the support body 12c to a position where the second anode (Cr anode) 12b is irradiated with the electron beam (second position). Further, by controlling the second movement mechanism 22, the controller 20 horizontally moves the first focusing element 13a to a position where the focusing action of the second X-rays by the second focusing element 13b arranged on the second Rowland circle C2 (FIG. 4) is not inhibited. Accordingly, the surface analysis of the sample S using the second X-rays is performed.

Hereinabove, the embodiment of the present invention has been described, but the present invention is not limited thereto as a matter of course, and various modifications can be made based on the technical idea of the present invention.

In the embodiment described above, for example, the Al Kα line are used as the first X-rays and the Cr Kα line are used as the second X-rays. However, the types of X-rays and anodes to be applied can be appropriately changed depending on the depth of an analysis to be required, the type of sample, and the like.

Figure 12:
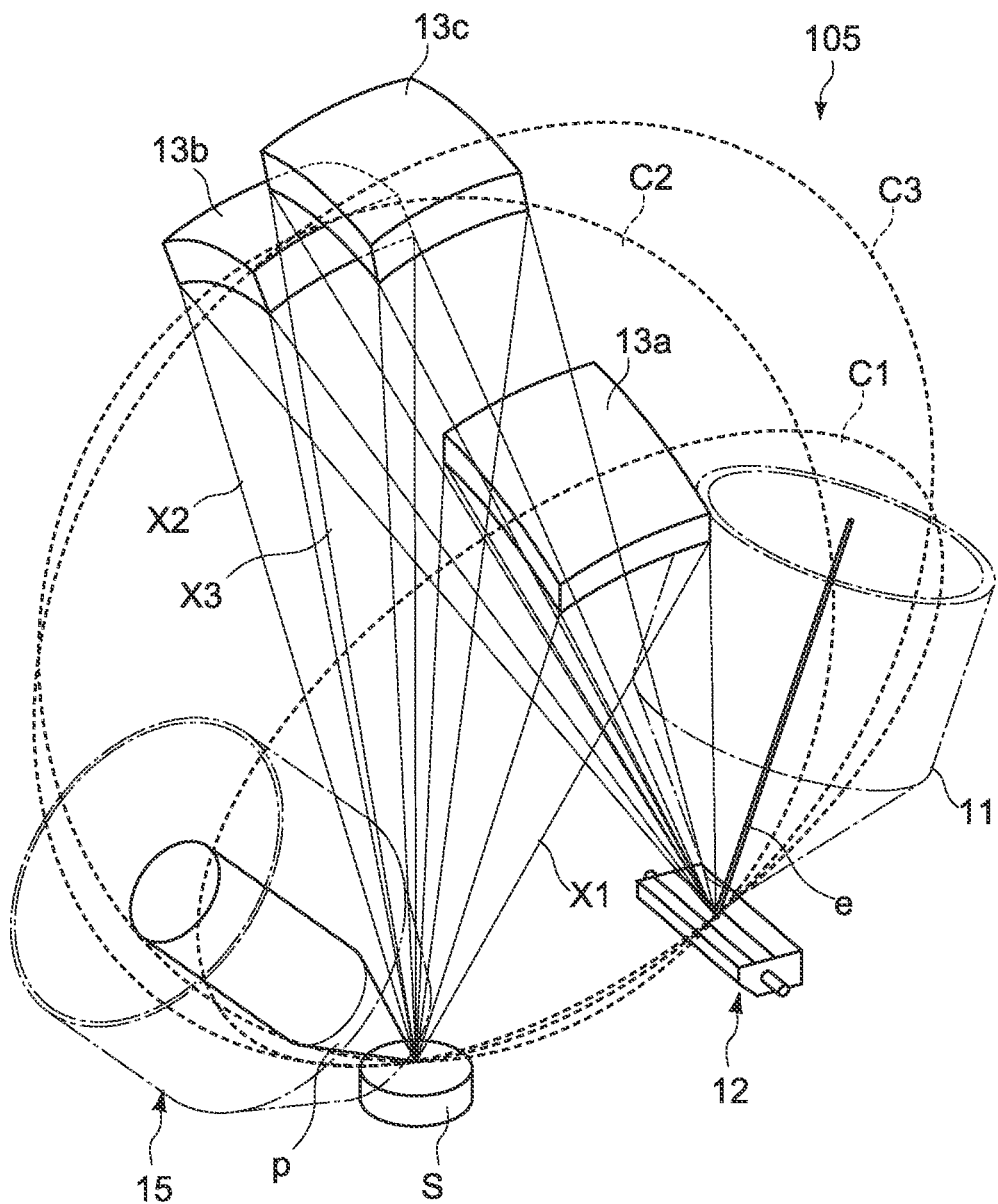
FIG. 12 A schematic perspective view of an X-ray irradiation device according to another embodiment of the present invention.

Further, in the embodiment described above, the two anode elements 12a and 12b are used as X-ray sources, but the number of X-ray sources is not limited thereto and may be three or more. In this case, the focusing elements may be additionally provided in accordance with the number of anode bodies, the type of X-rays to be generated, and the like as appropriate. FIG. 12 shows a schematic structure of an X-ray irradiation device 105 including a focusing mechanism having three focusing elements 13a, 13b, and 13c. The first focusing element 13a is arranged on a first Rowland circle C1 that passes through an anode 12 and a sample S. The second focusing element 13b is arranged on a second Rowland circle C2 that passes through the anode 12 and the sample S. The third focusing element 13c is arranged on a third Rowland circle C3 that passes through the anode 12 and the sample S. Accordingly, three types of X-rays having different wavelengths can be focused to the same focal position of the sample S.

Figure 13:
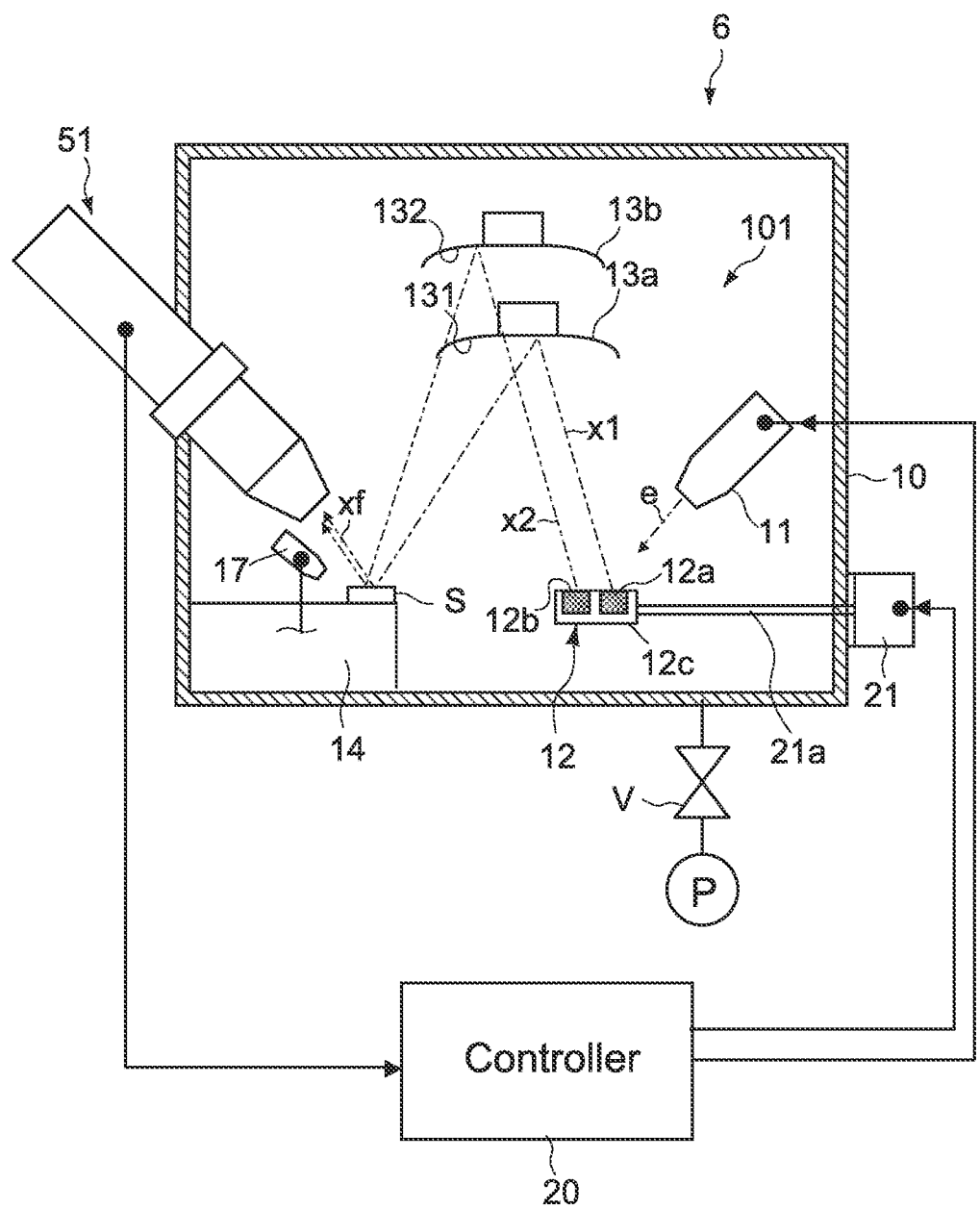
FIG. 13 A schematic structural diagram of an analysis device according to another embodiment of the present invention.

In addition, in the embodiment described above, the example in which the present invention is applied to the XPS device has been described, but the present invention is not limited thereto. The present invention is applicable to various types of analysis devices in which X-rays are used as a source of rays. For example, FIG. 13 shows a schematic structure of an X-ray fluorescence analysis device. An X-ray fluorescence analysis device 6 shown in the figure includes an X-ray irradiation device 101 and a photodetector 51. The photodetector 51 measures characteristic X-rays (fluorescence X-rays) (xf) that are emitted from the sample S by the sample S being irradiated with X-rays having different wavelengths. Further, in addition to the above, the present invention is also applicable to a photoelectron microscope that uses a photoelectron microscope instead of the photodetector 51.

DESCRIPTION OF SYMBOLS 1,2,3,4 analysis device (XPS device)
10 chamber
11 electron gun
11a deflector
12 anode
12a,12b anode element
12c support body
13a first focusing element
13b second focusing element
13c third focusing element
14 stage
15 analyzer
17 electron irradiation source
20 controller
21 first movement mechanism
22 second movement mechanism
101,102,103,104,105 X-ray irradiation device
131,132 mirror surface
S sample
E electron beam
p,p1,p2 photoelectrons
x1,x2 X-rays

The invention claimed is:

1. An X-ray irradiation device comprising:
a stage that supports a sample;
an electron gun that emits an electron beam;
an anode including:
a first anode element that generates a first X-ray having a first wavelength by being irradiated with the electron beam;
a second anode element that generates a second X-ray having a second wavelength different from the first wavelength by being irradiated with the electron beam; and
a support body that supports the first anode element and the second anode element;
a first X-ray reflecting mirror having a diffraction characteristic suitable for the first wavelength, the first X-ray reflecting mirror configured to focus the first X-ray to a focal position on a sample supported by the stage;
a second X-ray reflecting mirror having a diffraction characteristic suitable for the second wavelength, the second X-ray reflecting mirror configured to focus the second X-ray to the focal position; and
a controller selectively switching between a first state where the first anode element is irradiated with the electron beam, and a second state where the second anode element is irradiated with the electron beam.

2. The X-ray irradiation device according to claim 1, further comprising:
a first movement mechanism configured to be capable of moving the support body between a first position where the first anode element is irradiated with the electron beam and a second position where the second anode element is irradiated with the electron beam,
wherein the controller is configured to control the first movement mechanism to move the support body to the first position when the first state is selected, and
wherein the controller is configured to control the first movement mechanism to move the support body to the second position when the second state is selected.

3. The X-ray irradiation device according to claim 2, wherein the first X-ray reflecting mirror has a first mirror surface arranged on a first Rowland circle, the first Rowland circle passing an irradiation position of the electron beam to the anode and the focal position, and
wherein the second X-ray reflecting mirror has a second mirror surface arranged on a second Rowland circle, the second Rowland circle passing the irradiation position and the focal position.

4. The X-ray irradiation device according to claim 1, wherein the electron gun includes a deflector that is configured to be capable of switching an irradiation direction of the electron beam,
wherein the controller is configured to control the deflector to apply the electron beam to the first anode element when the first state is selected, and
wherein the controller is configured to control the deflector to apply the electron beam to the second anode element when the second state is selected.

5. The X-ray irradiation device according to claim 1, further comprising:
a second movement mechanism configured to be capable of moving the first X-ray reflecting mirror relative to the second X-ray reflecting mirror,
wherein the controller is configured to control the second movement mechanism to move the first X-ray reflecting mirror to a position where the first X-ray is focused, when the first state is selected, and
wherein the controller is configured to control the second movement mechanism to move the first X-ray reflecting mirror to a position where focusing action of the second X-ray by the second X-ray reflecting mirror, when the second state is selected.

6. An analysis device including the X-ray irradiation device according to claim 1 and an analyzer that detects energy emitted from a sample by irradiation with the X-rays from the X-ray irradiation device to analyze the sample, wherein the X-ray irradiation device has a focal position that is set as a position where the sample is placed.

7. The analysis device according to claim 6, wherein the analyzer is configured to detect kinetic energy of photoelectrons emitted from the sample.

8. The X-ray irradiation device according to claim 2, further comprising:

a second movement mechanism configured to be capable of moving the first X-ray reflecting mirror relative to the second X-ray reflecting mirror, wherein the controller is configured to control the second movement mechanism to move the first X-ray reflecting mirror to a position where the first X-ray is focused, when the first state is selected, and wherein the controller is configured to control the second movement mechanism to move the first X-ray reflecting mirror to a position where focusing action of the second X-ray by the second X-ray reflecting mirror, when the second state is selected.

9. The X-ray irradiation device according to claim 3, further comprising:

a second movement mechanism configured to be capable of moving the first X-ray reflecting mirror relative to the second X-ray reflecting mirror, wherein the controller is configured to control the second movement mechanism to move the first X-ray reflecting mirror to a position where the first X-ray is focused, when the first state is selected, and wherein the controller is configured to control the second movement mechanism to move the first X-ray reflecting mirror to a position where focusing action of the second X-ray by the second X-ray reflecting mirror, when the second state is selected.

10. The X-ray irradiation device according to claim 4, further comprising:

a second movement mechanism configured to be capable of moving the first X-ray reflecting mirror relative to the second X-ray reflecting mirror, wherein the controller is configured to control the second movement mechanism to move the first X-ray reflecting mirror to a position where the first X-ray is focused, when the first state is selected, and wherein the controller is configured to control the second movement mechanism to move the first X-ray reflecting mirror to a position where focusing action of the second X-ray by the second X-ray reflecting mirror, when the second state is selected.

11. An analysis device including the X-ray irradiation device according to claim 2 and an analyzer that detects energy emitted from a sample by irradiation with the X-rays from the X-ray irradiation device to analyze the sample, wherein the X-ray irradiation device has a focal position that is set as a position where the sample is placed.

12. An analysis device including the X-ray irradiation device according to claim 3 and an analyzer that detects energy emitted from a sample by irradiation with the X-rays from the X-ray irradiation device to analyze the sample, wherein the X-ray irradiation device has a focal position that is set as a position where the sample is placed.

13. An analysis device including the X-ray irradiation device according to claim 4 and an analyzer that detects energy emitted from a sample by irradiation with the X-rays from the X-ray irradiation device to analyze the sample, wherein the X-ray irradiation device has a focal position that is set as a position where the sample is placed.

14. An analysis device including the X-ray irradiation device according to claim 5 and an analyzer that detects energy emitted from a sample by irradiation with the X-rays from the X-ray irradiation device to analyze the sample, wherein the X-ray irradiation device has a focal position that is set as a position where the sample is placed.

\* \* \* \* \*